(12) United States Patent
Belalcazar

(10) Patent No.: US 8,435,193 B2
(45) Date of Patent: *May 7, 2013

(54) METHOD AND APPARATUS FOR IMPROVED CARDIO-PULMONARY RESUSCITATION

(75) Inventor: Hugo Andres Belalcazar, Kirkland, WA (US)

(73) Assignee: Hugo Andres Belalcazar, Kirkland, WA (US)

( * ) Notice: Subject to any disclaimer, the term of this patent is extended or adjusted under 35 U.S.C. 154(b) by 254 days.

This patent is subject to a terminal disclaimer.

(21) Appl. No.: 13/070,504

(22) Filed: Mar. 24, 2011

(65) Prior Publication Data

US 2011/0172572 A1    Jul. 14, 2011

Related U.S. Application Data

(63) Continuation-in-part of application No. 12/558,437, filed on Sep. 11, 2009, now Pat. No. 8,366,645.

(51) Int. Cl.
*A61H 31/00* (2006.01)

(52) U.S. Cl.
USPC .......................................................... 601/41

(58) Field of Classification Search .......... 601/41, 601/43, 44, 150, 151, 152
See application file for complete search history.

(56) References Cited

U.S. PATENT DOCUMENTS

| | | | |
|---|---|---|---|
| 4,397,306 A | 8/1983 | Weisfeldt et al. | |
| 5,551,420 A | 9/1996 | Lurie | |
| 6,425,393 B1 | 7/2002 | Lurie | |
| 7,226,427 B2 | 6/2007 | Steen | |
| 2002/0069878 A1 | 6/2002 | Lurie | |
| 2005/0165334 A1 | 7/2005 | Lurie | |

OTHER PUBLICATIONS

Chandra, Augmentation of Carotid Flow During Cardiopulmonary Resuscitation by Ventilation at High Airway Pressure Simultaneous with Chest Compression, American Journal of Cardiology, Dec. 1981, 1053-1063, vol. 48, Elsevier, USA. ( Pursuant to Rule 98(d), this reference is not enclosed since it was supplied in the parent case, U.S. Appl. No. 12/558,437 ).

Wilder, Methods of coordinating ventilation and closed chest cardiac massage in the dog, Surgery, Feb. 1963, 186-194, vol. 53, No. 2, Elsevier, USA. ( Pursuant to Rule 98(d), this reference is not enclosed since it was supplied in the parent case, U.S. Appl. No. 12/558,437 ).

Sanders, Failure of one method of simultaneous chest compression, ventilation, and abdominal binding during CPR, Critical Care Medicine, Aug. 1982, 509-513, vol. 10, No. 8, Williams and Wilkins Co, USA. ( Pursuant to Rule 98(d), this reference is not enclosed since it was supplied in the parent case, U.S. Appl. No. 12/558,437 ).

*Primary Examiner* — Patricia Bianco
*Assistant Examiner* — Raymond E Harris

(57) ABSTRACT

A cardio pulmonary CPR device and method provides enhanced circulation by an inventive sequence of states of chest compression and airway valve opening and closure. The embodiments of the invention produce enhanced circulation during cardiac arrest, while maintaining a degree of ventilation to the patient, including oxygen delivery in some embodiments. Some embodiments include mechanical compression units. Other embodiments include a compression sensor to detect manually delivered compressions.

14 Claims, 10 Drawing Sheets

METHOD AND APPARATUS FOR IMPROVED CARDIO-PULMONARY RESUSCITATION

CROSS REFERENCE TO RELATED APPLICATIONS

This patent application is a continuation-in-part of non-provisional patent application Ser. No. 12/558,437, filed on 2009 Sep. 11, which claimed the benefit of provisional patent application 61/096,316, filed on 2008 Sep. 12. The present patent application also claims the benefit of provisional patent application 61/316,979, filed on 2010 Mar. 24. Each of the non-provisional patent application Ser. No. 12/558,437, the provisional patent application 61/096,316, and the provisional patent application 61/316,979 are incorporated herein by reference.

FEDERALLY SPONSORED RESEARCH

None.

SEQUENCE LISTING

None.

BACKGROUND

This invention relates to the field of cardiopulmonary resuscitation. In particular, the invention provides improved devices and methods for enhancing blood circulation in patients undergoing cardiopulmonary resuscitation (hereon abbreviated as CPR). Such procedure is applied, for example, when cardiac arrest is present. In these situations, the heart ceases to pump blood out of the heart. To obtain some circulation until the normal pumping action of the heart can be restored, manual compressions are conventionally applied on the chest of the supine patient. The compressions on the chest may be alternated with brief periods of forced breathing into the patient, for example, by mouth to mouth ventilation. Alternatively, a ventilation bag with facemask or tracheal tube may be used to achieve the same effect. The American Heart Association publishes guidelines on CPR procedures. For example, the "2005 American Heart Association Guidelines for Cardiopulmonary Resuscitation and Emergency Cardiovascular Care", published in the Circulation journal, give a good overview of the subject of CPR.

While manual compressions are partially effective in providing circulation to the patient, it is not a perfect method. The manual compressions applied on the chest attempt to squeeze the heart and major vascular structures to eject blood into the extrathoracic arterial circulation. However, the rib cage provides an obstacle to achieve effective squeezing of the heart and vascular structures. The rib cage, in fact, spatially protects the internal organs including the heart from external forces. As a result, the physical frame forming the rib cage attenuates the amount of squeezing on the heart obtained by external compressions on the chest, by distributing the force across entire chest and rib cage.

Furthermore, when a rescuer provides CPR and compresses the chest of the patient, the heart only experiences a partial squeeze, because soft tissues surround the heart and mediastinum. Namely, the soft tissues are the lungs on the sides of the mediastinum, and inferiorly, the soft tissues of the upper abdomen. As the external compression is delivered, the heart deforms and expands part of its volume into the surrounding soft tissues. This expansion creates inefficiencies in squeezing the heart during CPR. It would be desirable to impede that lateral expansion into soft tissues so that a more effective cardiac squeeze is achieved. One such method to effectively accomplish such lateral support is open chest cardiac massage, in which clinicians manually squeeze the heart with their hands. In this case the squeeze of the heart is delivered around most of the heart's perimeter, not just the front and back as in traditional CPR. The squeeze is therefore very effective, but it of course requires a very invasive surgery to expose the heart, and is thus not amenable to typical CPR and first aid situations. In any case, the point emphasized here is the inefficiency of the squeeze of the heart due to its laterally surrounding soft tissues and its protective rib cage, as provided by conventional CPR methods.

In an effort to alleviate some of the above shortcomings, and to enhance circulation during CPR, several devices have been proposed in prior art. For example, U.S. Pat. No. 5,551,420 to Lurie describes a special valve coupled to the airway of the patient, such that the flow of air into the patient's lungs is restricted during the chest decompression phase of CPR. The valve's restriction of air inflow into the patient's lungs, in combination with the natural elastic recoil of the chest after a compression, causes a negative intrathoracic pressure. This vacuum helps draw venous blood from the body into the thorax prior to the next chest compression, thereby better priming the heart pump with enhanced filling. As a result, more blood is in the heart when the next compression occurs, and therefore, more blood is ejected, obtaining enhanced circulation.

In the above cited '420 patent, Lurie also mentions the use of positive pressure, by implementing a restriction to outflow of air from the patient's lungs during the compression phase of CPR. It can be appreciated that if the airway is restricted to outflow, greater intrathoracic pressure will be obtained during a compression step of CPR. Such enhanced pressure will help develop a more efficient ejection of blood from the heart. This addresses the inefficiency of cardiac expansion of the heart into surrounding soft tissues during external compression. Because the lungs cannot readily evacuate their air due to the outflow restriction, the heart is laterally impeded from expanding into the lung spaces. This contributes to a more effective squeeze of the heart when applying external compression to the front of the chest.

The prior art however does not describe a sequence, nor a device to provide it, that would combine optimized positive and negative pressures. Furthermore, when passive decompression CPR is used according to the known art, there is a disadvantage when providing inflow air-resistance during more than a few compression cycles. The distinction of active and passive decompression in CPR merits explanation at this point. By passive decompression CPR it is understood that no active devices are used to expand the chest after each compression step, for example, by using suction cups on the skin to pull and expand the chest. In passive decompression CPR, the chest is allowed to naturally and elastically recover in shape after each compression. The discussion below, and for the rest of this document, is framed in the context of passive decompression CPR, which is the most commonly used method.

Describing the disadvantage in more detail, when using the known inflow restriction devices, there will be less air exchange occurring than there would be if no air restriction was present. In consequence, there will be less air volume present in the lungs just prior to the compression phase of CPR. In other words, after a few compression-decompression cycles, the patient's chest will hold less air volume at the end of the chest decompression phase, due to the impediment presented by the special valve, which restricts the filling of the lungs. Air is easily ejected from the lungs with chest compression and an open airway, but not so easily inhaled through the restrictive valve. Therefore, the chest will not inflate fully to its natural relaxed state. This volume deficiency will be greater if the cracking pressure is set to a higher value on the inflow restriction valve. The cracking pressure is the pressure at which the valve will open to allow air inflow to the lungs, when the valve is subjected to negative pressure at the patient airway side. It can also be understood as the amount of inflow resistance. It must be properly set for the particular patient, as a child, for instance, may have different negative pressure requirements than a large adult.

The extreme situation of lung air volume reduction occurs with a very high cracking pressure: the air inflow is completely occluded when the chest attempts to expand during the decompression phase of CPR, and no new air enters the chest. Notice that this happens even the though the elastic recoil of the chest creates a relatively high vacuum to draw blood to the heart from the periphery. So while blood is adequately drawn into the chest by vacuum, it is done at the expense of air intake.

The disadvantage noted above has two implications: first, barring manually delivered ventilations, which defeat the negative pressure advantages, there is less respiratory gas exchange with the outside atmosphere than in traditional open airway CPR, so oxygen and carbon dioxide transport is negatively affected. Second, if a device or method were to simply combine vacuum with a positive pressure technique as described earlier (restricting air outflow during chest compression to enhance ventricular blood ejection), it will be less effective. This inefficiency of the compression phase any such simple combination has not been noted in the prior art. The inefficiency occurs because, with the reduced volume of lung air present at the beginning of the chest compression, the heart and major vessels can more easily deform and expand into the less inflated lung space. In contrast, if the precise states of the lungs and heart were taken into account, for example, if the lungs were instead optimally full of air, and the outflow of air restricted during chest compression, the squeeze on the heart would be enhanced, as inflated lungs present a better lateral obstruction to the heart, than do deflated lungs. Such is one of the objectives of the invention. Similarly, if a vacuum were to be applied without regard to the prior states of the cardio-pulmonary system, the benefit of the negative pressure may not be optimal. Therefore, an optimized combination of vacuum and positive pressures is sought in order to further enhance cardio pulmonary circulation. Further, it would be desirable to accomplish such combination without significantly impairing ventilation of the patient. What is also needed is a device and method that optimally provides both negative and positive intrathoracic pressures to enhance circulation during CPR, but does so while maintaining a degree of gas exchange that does not substantially defeat the assistive thoracic pressures.

The invention embodiments described in this document address these needed characteristics, while offering further advantages, and will therefore provide for enhanced CPR devices and methods.

SUMMARY

In a general aspect, the invention consists of a valve disposed on a facemask, ventilation bag, tracheal tube, or any similar airway control apparatus. The invention includes electronic or mechanical control of the valve, so that it completely closes the airway of the patient, during some compression and decompression phases of CPR, and completely opens the valve at other compression-decompression phases. By completely occluding the airway, and coordinating compressions and decompressions with the air status of the lungs, the present invention provides maximum vacuum and maximum positive pressures in the thorax, assisting the priming and ejection of the heart's pumping action during CPR. Similarly, by completely opening the airway, the invention provides for maximum respiratory gas exchange. The invention includes electronic circuits and mechanical systems to sense the compressions and decompressions given by the rescuer. An electronic control unit then uses that information to produce a particular sequence of opening and closing of the valve, in synchrony with the compression-decompression information. In one embodiment, the control unit of the invention produces at least five sequential and distinct compression-valve-lung states, that are repeated in the following manner and order: a) compression with closed airway and full lungs; b) decompression with closed airway and full lungs; c) compression with open airway and emptying lungs; d) decompression with closed airway-empty lungs; e) pause with open airway-filling lungs; and then back to a). According to this embodiment, a rescuer using the inventive device can simply be instructed to deliver compression pairs with a brief intervening pause. In this way, the said five state sequence will be realized.

In another embodiment, the invention additionally provides mechanisms and circuits for active positive pressure ventilation of the lungs. The control unit coordinates this so it occurs during step e) of the above sequence.

In yet another embodiment, the invention includes a chest compression unit that automatically delivers mechanical compressions to the patient, relieving the need for a human rescuer to deliver compressions. This embodiment controls the airway valve in accordance to an inventive synchronization, without the need for a compression sensor.

Accordingly, advantages include the provision of maximum vacuum and maximum compression on the heart during CPR, while at the same time nearly maintaining respiratory gas exchange of traditional CPR. Further, the devices and methods described herein accomplish this cardiopulmonary enhancement without the need to be concerned of specific cracking or threshold pressure values of airflow valves. Still further advantages will be apparent upon studying the following description and accompanying drawings.

DRAWINGS

DETAILED DESCRIPTION

Figure 1:
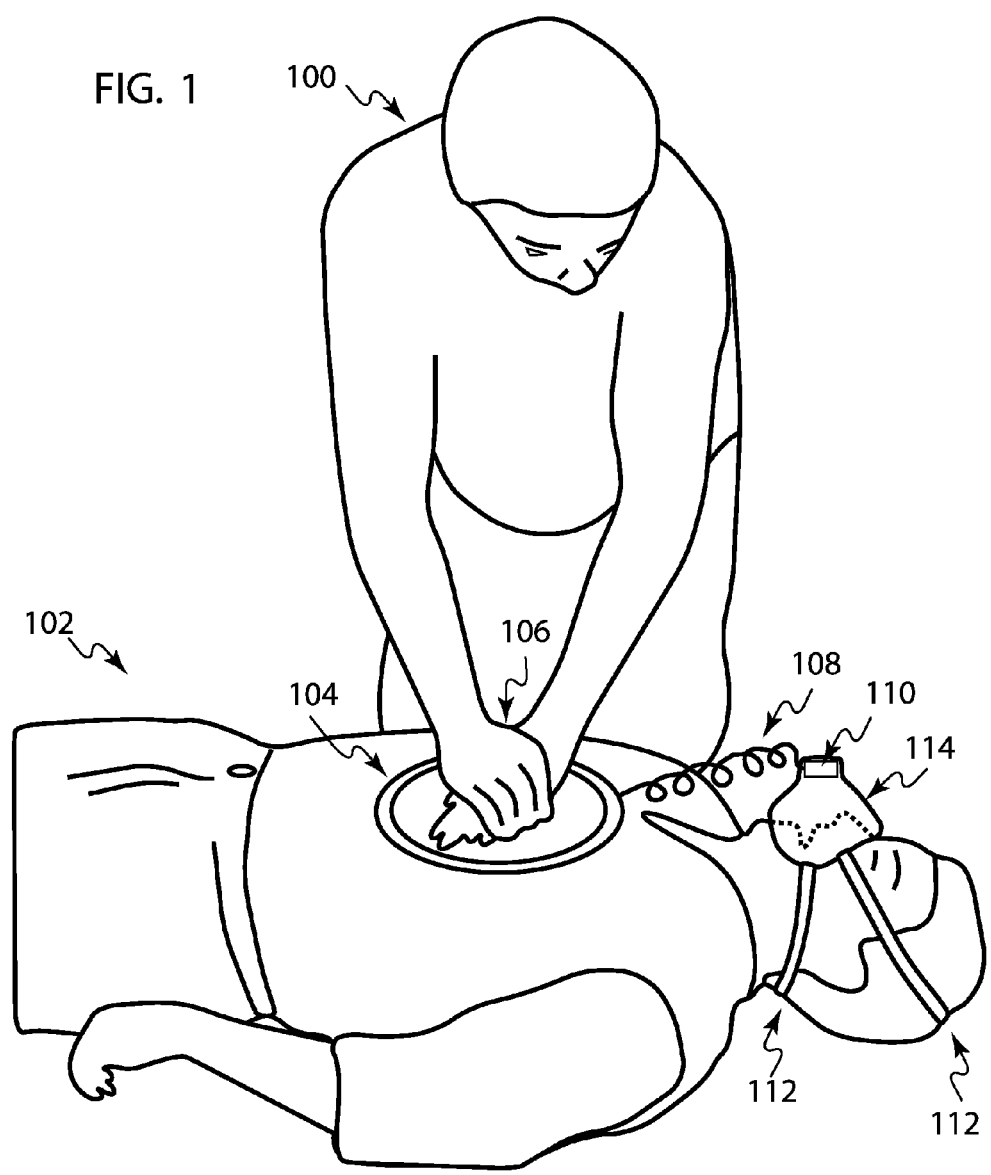
FIG. 1 shows an embodiment of the invention being used to administer CPR on a patient.

FIG. 1 shows a rescuer 100 and a patient 102 who is undergoing cardio-pulmonary resuscitation (CPR). It is noted here that the term CPR also includes the mode of resuscitation where no ventilations, (by mouth-to-mouth, bag, or otherwise), are given to the patient. For example, cardio-cerebral resuscitation (CCR), is understood throughout this document to be also included when the term CPR is used. As is well known in the field, rescuer 100 uses his/her hands 106 to press against the chest of patient 102. In accordance to one embodiment of the invention, a compression sensor 104 is placed on the chest of the patient. Rescuer 100 delivers the chest compressions through compression sensor 104 to the chest of the patient. Compression sensor 104 is sized and formed, preferably in a flattened manner as shown in FIG. 1, to be placed on the chest of the patient 102. It is constructed preferably of a material that will not slide easily off the patient 102. Suitable materials include, but are not limited to, rubber, latex, silicone, and the like. Compression sensor 104 operates to receive the force of the hands 106 of the rescuer 100, and transmit it to the patient 102, in a manner consistent with conventional CPR. In order to accomplish the function of sensing of compressions and decompressions, sensor 104 may include a switch operable by the force delivered by the rescuer 100. When the hands 106 press downward and deliver a compression to the chest of patient 102, the switch may close an electric circuit, signaling the beginning of compression. When the force on the chest of the patient is relieved during the decompression phase of CPR, the switch opens, signaling the beginning of said phase. Other forms of sensing the force of the rescuer 100 on the patient 102 may be used, as is known conventionally in the field of electrical and mechanical engineering. For example, sensor 104 may be constructed using a capacitive design, where two conductive plates or membranes separated by a dielectric are used. A separate electric circuit may be used to sense the change in capacitance and indicate a compression. Said switch, conductive plates, or conductive membranes constitute sensor means to sense compressions on the chest of the patient. Other similar means can be used, including magnetic, resistive, pneumatic, or others as known in the electrical and mechanical arts. In the pneumatic instance, sensor 104 can be constructed as a flattened rubber bellows. As such, it expels air every time it is compressed. Such air can be conducted by a hose conductor 108 to the facial mask, to be used as a synchronizing signal, as will be further described below, in accordance to this invention. The sensor 104 embodied with a bellows may also include a one way intake air valve, and a recoil spring, to achieve re-inflation after each compression.

Describing further elements and function of the invention, the information or signal of compression or decompression given by hands 106 of the rescuer 100 is transmitted via a conductor 108 to an air flow control assembly 110 that forms part of a facial mask 114. Facial mask 114 is coupled to the face of the patient 102 with straps 112 so as to achieve a near or complete air seal. In this manner, air flow control assembly 110 either opens or occludes in a complete or nearly complete manner the airway of the patient, thereby exclusively controlling the ventilation and airflow to and from the lungs of the patient 102. Thus facial mask 114 constitutes a sealing means to control the airway of the patient. Using an inventive and advantageous sequence synchronized with the chest compressions, said patient air flow is controlled so as to provide enhanced cardiopulmonary circulation of blood. Such inventive sequence will be further described later in this document.

Simple electrical wires can realize conductor 108 of FIG. 1. In the embodiment of sensor 104 that includes an electric switch, a pair of electric wire conductors are coupled to the switch, and therefore convey the state of the switch to air flow control assembly 110. Alternatively, sensor 104 is capacitive, and conductor 108 could include at least two wires to couple the capacitance to airflow control assembly 110. Alternatively, conductor 108 can be a semi-rigid rubber or plastic hose that conveys air or liquid pressure squeezed from a similarly filled bellows sensor 104. As an even further alternative, conductor 108 can be eliminated if wireless methods of signal transmission from sensor 104 to airflow control assembly 110 are used. As will be apparent to those skilled in basic techniques of electrical and mechanical engineering, alternative sensor and signal conduction devices are possible without departing from the spirit of this part of the invention. That is, to detect when chest compression and decompressions occur, and to deliver such signal to the airflow control assembly 110.

In one embodiment, conductor 108 may also include electric conductors to supply electrical power to airflow control assembly 110, when an energy source, such as a battery is used. Such battery may be included in sensor 104, or further distally coupled to it via other conductors (not shown) that could lie beside the patient 102. Alternative battery sources and arrangements are easily apparent to those skilled in the electrical arts, and may be included within various components of the invention, without departing from its scope.

Figure 2:
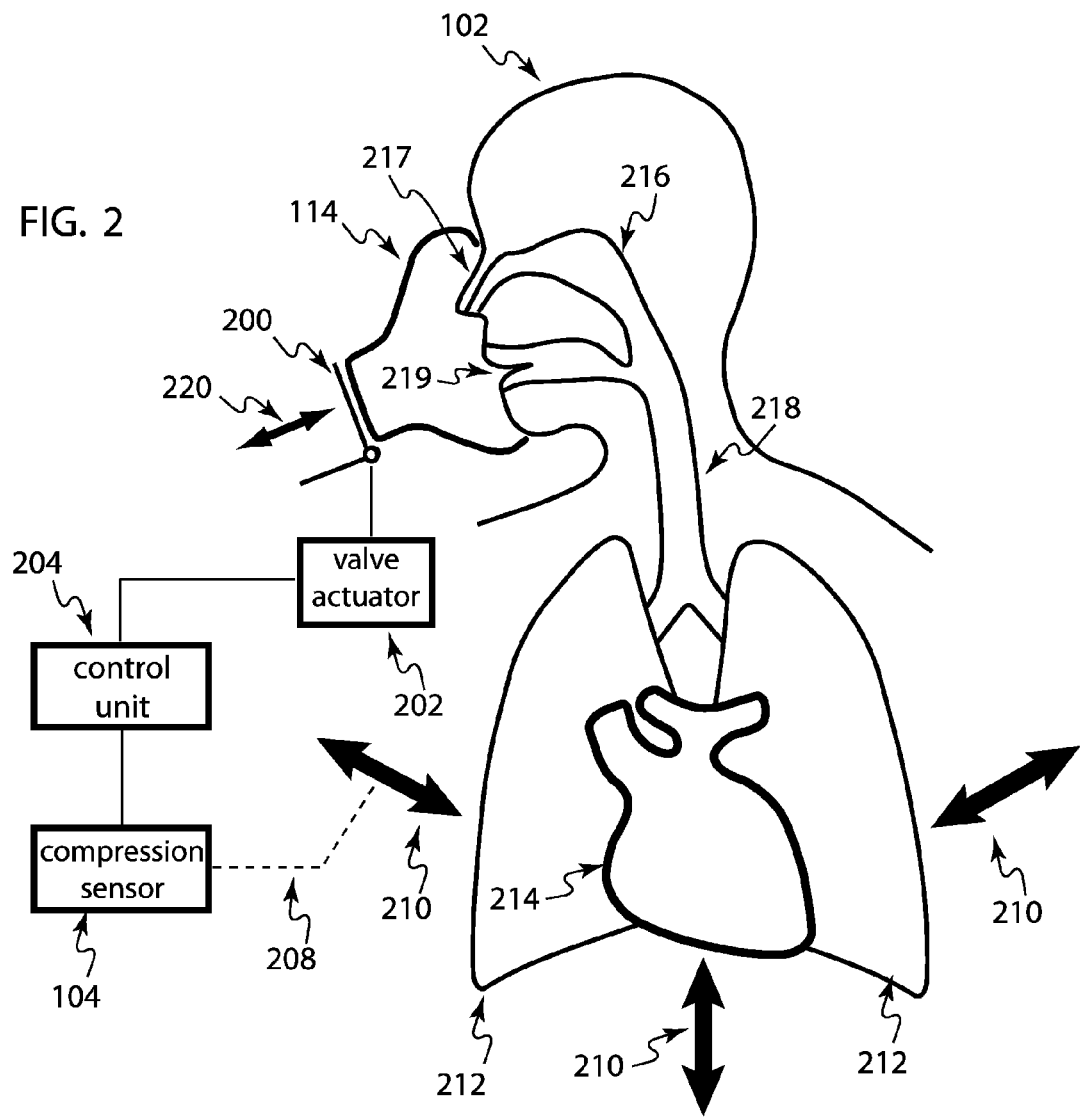
FIG. 2 shows the elements of this invention, when embodied with a facemask.

FIG. 2 illustrates in block diagram form the invention embodied with a facial mask 114 coupled to patient 102. Control of the upper airway 216 and lower airway 218 is established with the mask 114 covering nose 217 and mouth 219, and by ensuring an air seal against the facial skin of the patient 102. Such air seals and mask construction is conventionally known in the field of anesthesia, emergency medicine, and the like. However, the present invention includes a valve 200, that is inventively controlled, either to close or open the flow of air 220 to and from the patient's respiratory system. Valve 200 is operated to open or close via valve actuator 202. Valve 200 may be embodied in various forms for the purposes of this invention, for example, by a flap occluding a tube passage way, a needle plunger against a hole opening, or any other pneumatic valve method known to those skilled in the art of air flow control for medical devices. Actuator 202 may be a solenoid, a servo, a pneumatic piston system, or any other conventional pneumatic valve activation system. These constitute means to actuate the valve 200.

Control unit 204 provides the signal or energy to actuator 202, so that valve 200 opens and closes at the appropriate times, inventively synchronized and sequenced according to the invention, as will be further described below. Compression sensor 104 senses when forces 210 are applied to the thorax of the patient during the CPR procedure. Dashed line 208 shows this sensing relationship. The information from sensor 104 is coupled to control unit 204, so it can achieve the inventive synchronization and sequence of control of valve 200, as will be later described herein.

Control unit 204 may be implemented in various ways known to those skilled in the art of electrical control. In one embodiment of this invention, a microprocessor or microcontroller may be used. The miccrocontroller or microprocessor may include at least one timer and at least one memory storage location to save timing information. The microcontroller may also include an arithmetic unit to provide basic mathematic computations, and basic signal processing techniques, as is generally known in the art of microprocessor based medical devices. Alternatively, a simpler non-program based sequential circuit can be used, using sequential electronic circuits could be used. In another implementation, an analog electronic circuit could be constructed to provide the required control signals to valve 202.

The functional blocks shown in FIG. 2 can be variously located, achieving in all cases the objectives of the invention. For example, the compression sensor 104 may physically include the control unit 204. In a flattened bellows embodiment of the sensor 104, the control unit can be included as a circuit inside the bellows. Alternatively, control unit 204 may be instead included as part of mask 114. For instance, control unit 204, valve actuator 202, and valve 200 may all be included in one assembly, the airflow control assembly 110 illustrated in FIG. 1. Other physical dispositions of the functional blocks 104, 204, 202, and 200 may be used, without departing from the spirit of the invention.

FIG. 2 also shows the lungs 212 of the patient 102, shown here in an undefined and general inflation state. As will become apparent further below, the amount of air inflation of lungs 212 is an important factor in the operation of the invention. Heart 214 is also shown in a general undefined state of ventricular blood filling. As will also become apparent later in this description, the amount of ventricular blood filling of heart 214 is another important factor in the operation of the invention. Thoracic compression and decompression forces 210 typical of CPR are shown as they relate to the lungs 212 and heart 214.

Figure 3:
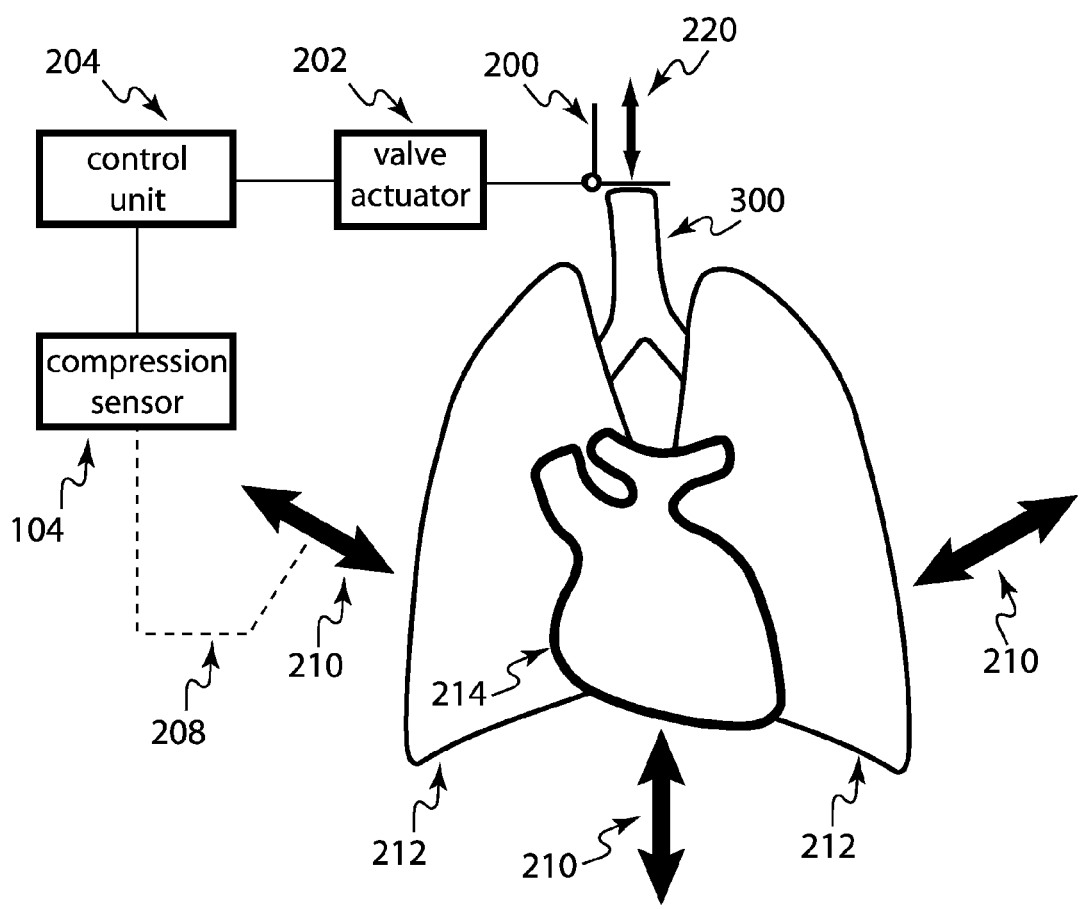
FIG. 3 shows in a more general manner the elements of this invention, when embodied with a valve located anywhere along the patient's airway.

Similar to FIG. 2, the diagram in FIG. 3 more broadly describes the invention by showing that it can be embodied with an airway valve 200 located anywhere as long as the flow of air 220 from the lungs 212 of the patient is controlled. The airway 300 of the patient 102 is shown here as the trachea. As such a tracheal tube could include valve 200, provided a good air seal is achieved so that exclusive control of airflow is made by valve 200. Other locations of the valve 200 can be used and still be within the limits of the invention. For example, the valve could be on a mouthpiece, as part of an upper airway device, or other airway devices know to those skilled in the art of medical artificial ventilation. Besides this generalization of airway control, all labels and functional blocks are as noted for FIG. 2. Thus, said tracheal tubes and upper airway devices constitute known sealing means to control the airway of the patient.

FIGS. 4A-4E and FIG. 5. show the five state sequence of cardio pulmonary states achieved with this invention. The states are labeled with numerals 401 to 405, and are shown in FIGS. 4A-4E, respectively. These five states are also shown at the top of the timing diagram of FIG. 5, and correspond to the events shown in the traces below them. Throughout this document it is clear that these states follow that sequence in order, from, 401-405 in sequential order, and then recommence again with 401, then 402, 403 and so on continuously, for the duration of the CPR procedure. The inventive device enables that advantageous sequence, with each state having a particular cardio pulmonary and valve condition.

In the following detailed description, FIGS. 4A-4E and FIG. 5 will both be referenced to explain the operation of the inventive device, and its advantages. Beginning with the description of state 401 in FIG. 4A, the invention provides for a closed airway valve 200 during the application of CPR thoracic compression 411. In this state 401, the lungs 212 are inflated to the maximal inflation amount, as previously achieved in the preceding decompression of the chest with an open airway, namely state 405. In this description of the inventive cardiopulmonary sequence, the term "maximal inflation" is in the context of CPR, and therefore does not refer to the maximal inflation achieved for example by a large voluntary inhalation, that is, a conscious vital capacity inflation, as is known in conventional respiratory physiology. In the case of passive decompression CPR, where after a compression the chest naturally re-expands due to the elastic recoil of the rib cage and thorax, the maximal inflation refers to the amount of air present in the lung at the end of such recoil with an open airway. As can be easily discerned, such inflation will be greater if the airway is widely open. In the prior art, airflow restriction devices may prevent full inflation of the chest. In contrast, in this invention, the state 401 has more air because it was preceded by a decompressed state 405 with an unrestricted airway.

In some embodiments, even more air could be present if active lung inflation structures are provided to act during state 405, for example with a bag, or a mechanical ventilation device, as is known in the art of artificial ventilation for patients.

Figure 4A:
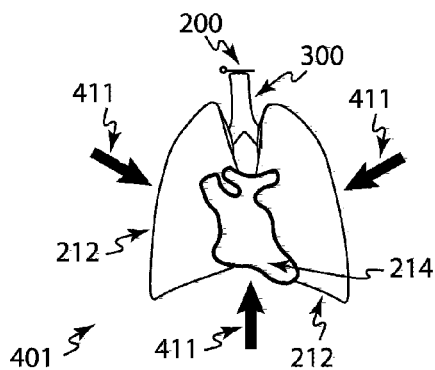
FIG. 4A shows the first state in the sequence of operative states of the cardio-pulmonary system and the airway valve, achieved with the invention.

With that distinction from prior art, FIG. 4A shows state 401 where the lungs 212 are maximally inflated and the airway is occluded completely by closed valve 200. A CPR compression 411 is delivered. Because the airway is occluded in this state 401, and the lungs 212 are maximally inflated, the compression force is best transmitted to the heart's ventricles and a maximal ejection is achieved. Again, here "maximal" refers to the context of all possible ejections that can be achieved during CPR. As will become apparent, the reason for this maximal ejection is that the heart was filled by a maximal intrathoracic vacuum in preceding state 404. Further, the greater lung inflation of lungs 212 provide better lateral mechanical support in squeezing the heart. If the lung inflation was less, the heart would more easily expand into the lateral spaces when the chest is compressed in the antero-posterior direction. Such is one advantage of this invention: a compression with maximally inflated lungs providing better lateral support to the heart. Heart 214 is thus drawn in state 401 as maximally squeezed, as compared to the other states.

Figure 5:
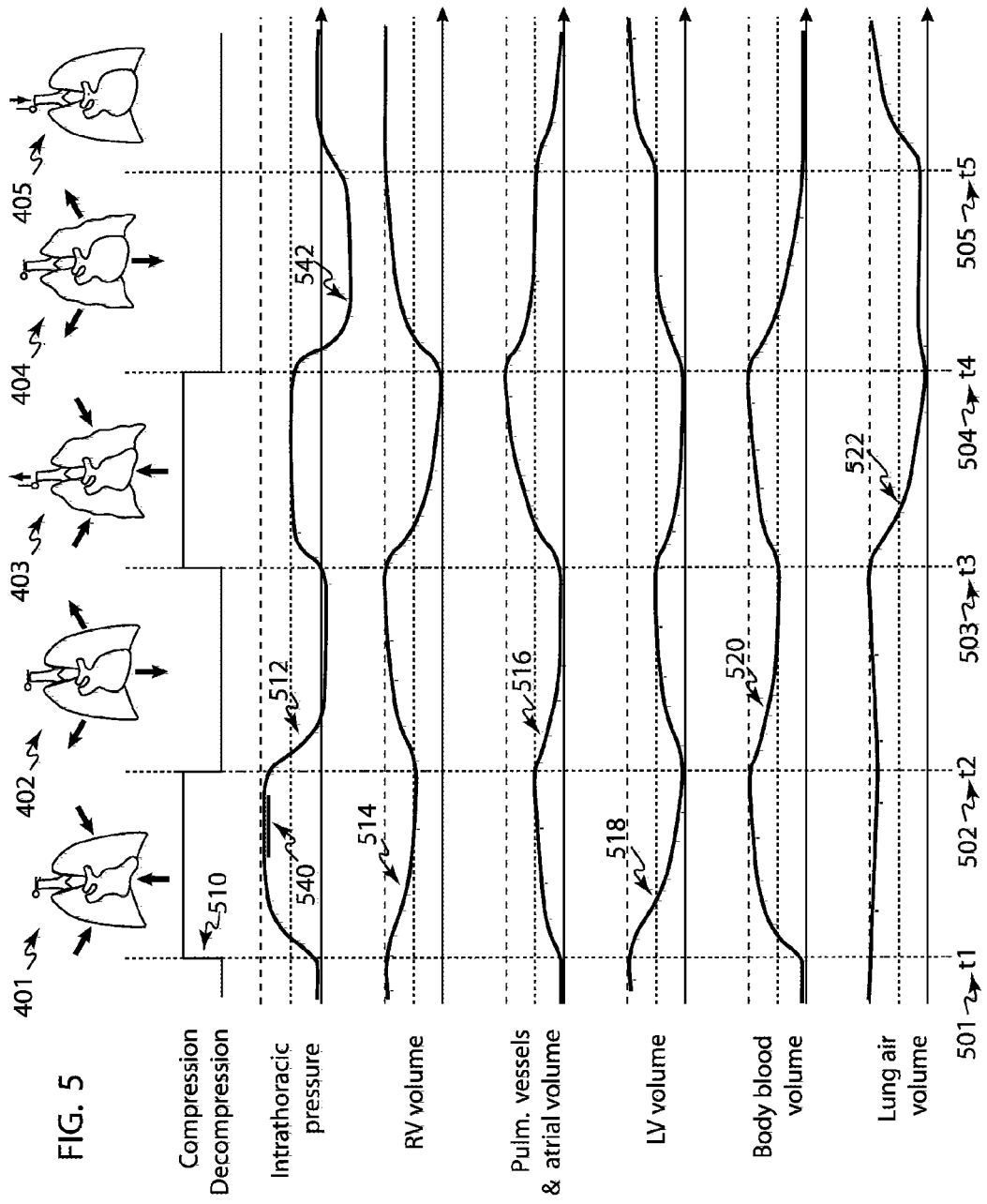
FIG. 5 shows in greater detail the inventive sequence of intrathoracic pressures, cardio-pulmonary cycles, and airway valve states.

Now referring to FIG. 5, the intrathoracic pressure and cardio pulmonary volumes are shown during each state. Trace 510 shows the timing of application of chest compressions and decompressions during the CPR procedure. The passage of time proceeds to the right in a conventional manner. The instants of time when the states change are marked t1 through t5 at the bottom of the figure, and labeled with numerals 501 through 505 respectively. Circulating blood volumes in the various compartments of the circulatory system are shown in traces 514, 516, 518, 520. These volumes represent only the differential circulating blood volume, not the total blood volume of the compartments. It can be appreciated that as the pumping of blood occurs, blood moves from one compartment to the other, with some elastic storage occurring in the various components. For instance, in a normal conscious individual, a differential blood volume in circulation can be 70 milliliters (ml), a typical ventricular volume ejected by the heart, and stored in part in the arterial compliances. In contrast, the total absolute blood volume in the body can be about 5 liters. This clarifies the concept of differential versus absolute blood volumes of the circulation that are used in this document.

In all of the following discussions reference is only made to this differential concept of blood volumes in the circulation. Accordingly, in FIG. 5, and as an exemplary description in a typical adult patient, each vertical axis division marked by horizontal dashed lines represents about 50 ml of blood. Illustrating the use of the vertical scales, in state 401, the body blood volume 520 gains 100 ml as a result of a chest compression causing a maximal left ventricular ejection between the times t1 501 and t2 502, whereas the right ventricle ejects 50 ml, as seen in trace 514 during the same period of time.

The sum of the differential circulating volume of blood remains constant when added across all compartments, as no new blood is being created, of course. If one adds the exit volumes of all traces 514, 516, 518 and 520 at any instant of time t1, t2, t3, t4, t5 (labelled 501 to 505), one obtains a constant volume of 400 ml, in this example.

It is noted that these scales and volume quantities are illustrative only, and serve in the following description to explain the operation of the invention. Different quantities may appear in practice with the varying size of individuals, so that the use of specific quantities below should not be construed as a limitation of the invention.

Traces 514, 516, and 518 refer to the cardio pulmonary circulating blood volumes, as labeled in FIG. 5. Trace 520 refers to the balance of the circulating blood, in the rest of the body, and excluding the heart and lungs. Trace 522 is an air volume trace denoting volume of in the lungs 212.

Returning to the cardiopulmonary advantage discussion, and looking in FIG. 5 at state 401 in, and below it, the intrathoracic pressure 512 and all the volumes 514-520, one can appreciate that the intrathoracic pressure 512 is maximal during state 401, at about time 540. There is maximal left ventricular (LV) ejection as noted in trace 518, when the left ventricle ejects 100 ml maximally aided by a chest compression enhanced by inflated lungs and a closed airway. The right ventricle (RV) also ejects, but not nearly as effectively, because it must eject into a more resistive load: the relatively and positively pressurized lung. As such, trace 514 shows a moderate RV ejection of 50 ml during this state 401. Such ejection is mostly received by the pulmonary vessels, (pulmonary arteries and veins), as well as the left atrium, as noted in trace 516.

Figure 4B:
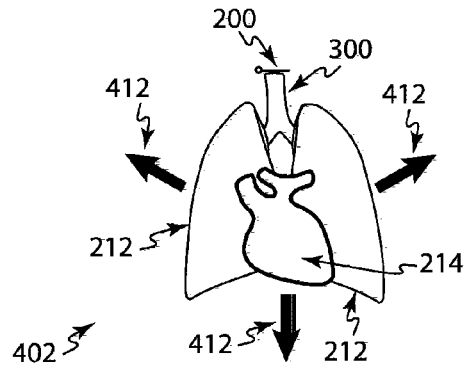
FIG. 4B shows the second state in the sequence of operative states of the cardio-pulmonary system and the airway valve, achieved with the invention.

Continuing to the second state 402 in FIG. 4B, the chest is decompressed during the decompression phase of CPR. In this state the invention's control unit 204 and airway valve 200 provide for a closed airway. Because no air has been expelled from the thorax in states 401 or 402, the chest recoil of decompression state 402 will provide a moderate, not maximal, amount of intrathoracic vacuum. Since the lung is more full of air, some of the vacuum created by the passive recoil is absorbed by expansion of the greater air volume in the lungs. Therefore, this decompression does not offer as much intrathoracic vacuum as would be afforded if the lungs had less air to expand in the vacuum. That is why the vacuum is qualified as moderate in this description of state 402, and the heart 214 is illustrated in FIG. 5 with moderate filling: 50 ml enter each of the RV and LV as noted in traces 514 and 518, respectively. These volumes drain from the lung, atria, and body as evident in traces 516, 518, and 520.

Figure 4C:
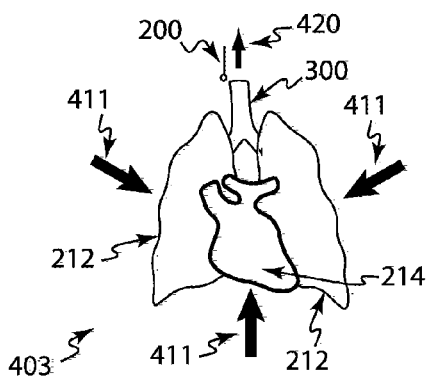
FIG. 4C shows the third state in the sequence of operative states of the cardio-pulmonary system and the airway valve, achieved with the invention.
Figure 4D:
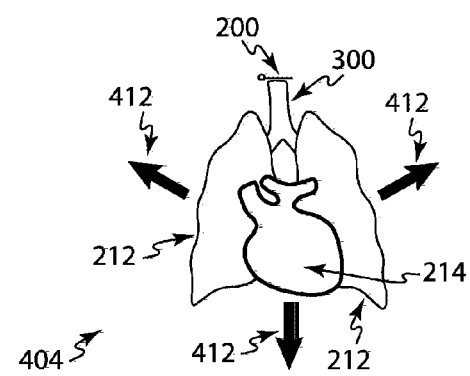
FIG. 4D shows the fourth state in the sequence of operative states of the cardio-pulmonary system and the airway valve, achieved with the invention.

Continuing now to the third state 403 in FIG. 4C, a chest compression delivered by a rescuer 100 applies compression 411 to the thorax, while the inventive device opens the airway valve 200 at instant t3 503 on trace 510. This happens when the sensor 104 and control unit 204 detect the beginning of a second compression in the five state CPR cycle, and therefore actuate the airway valve 200 via actuator 204 to an open position. In this state 403, a maximal RV ejection of 100 ml occurs as it ejects into a low air volume and open air way coupled lung. That is, the RV ejects its relatively high volume into a lower resistance load. The received high volume primes the pulmonary circulation and atria with a maximal differential blood volume of 100 ml, as noted in trace 516, at instant t4 504. Further, the compression 411 and open airway evacuate air 420 from the lungs to provide ventilation to the patient. This differential air evacuation can be seen in FIG. 5 trace 522. As will be apparent in the next state 404, this near maximal evacuation of the lung air will improve circulation by maximizing the vacuum 542 in the lungs 212.

Continuing now to the fourth state 404 in FIG. 4, the sequence continues when the inventive device detects via sensor 104 the end of compression and the beginning of decompression at instant t4 504. At that instant, the airway valve 200 is closed, and the chest, relatively devoid of air from the prior state 403, recoils and passively expands to create a vacuum in the thorax. This is noted in FIG. 5 trace of intrathoracic pressure 512, where a maximal negative pressure, i.e. a vacuum, is achieved at 542. This vacuum, provided via a completely closed airway valve 200, provides the maximum vacuum that can be achieved via passive chest recoil. This is in contrast to prior art, where there is a partial restriction to the ingress of air, such that some vacuum is created, but not as great as when a complete occlusion of the airway is applied with a more empty lung. The greater vacuum further enhances the circulation by drawing more blood into the heart 214 from the lungs 212 and body. Such volume transfers during this high vacuum state 404 are noted in FIG. 5, in traces 514, 516, 518, and 520. The thoracic vacuum contributes to pull 100 ml from the body into the right side of the heart mostly, as seen in body volume trace 520 losing 100 ml, and the RV gaining 100 ml, as evident in trace 514. The pulmonary vessels and right atria, (trace 516), subject to vacuum, and thus have more difficulty surrendering volume into the left ventricle, which only gains 50 ml (trace 518) during this vacuum state.

Figure 4E:
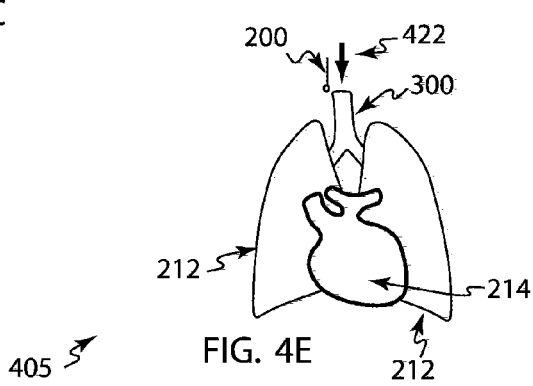
FIG. 4E shows the fifth state in the sequence of operative states of the cardio-pulmonary system and the airway valve, achieved with the invention.

Continuing with the final state of the cycle, state 405 in FIG. 4E and FIG. 5, the inventive device opens the airway valve at instant t5 505 in FIG. 5. This is a "pause" state in the CPR cycle proposed with this invention. It allows for intake air 422, facilitated by the intrathoracic vacuum created in the previous state 404, and a completely open airway. The inflow of air is noted in trace 522 of FIG. 5, after time t5 505. The entering pulmonary air, and the elastic compliance of the pulmonary arteries recoiling from a lung vacuum, contribute to push blood forward towards the left side of the heart. In this example, about 50 ml of volume are added to the LV in this state 405. This is evident in lung vessels and atria trace 516 of FIG. 5 losing 50 ml for the benefit of the LV, trace 518.

The enhanced air inflow of this state 405 is in contrast to some prior art devices that enhance circulation with vacuum, but do not include a regular and periodic passive ventilation cycle with unrestricted airways as part of the CPR device. Whereas the prior art restrictive devices require interrupting the CPR or the vacuum creation to deliver occasional ventilations, the present invention has the advantage of including ventilation as part of the CPR cycling routine, without imposing significant pausing or interruption of either compressions or vacuum creation. The disadvantage of interruptions for ventilation delivery has been noted by, for example the March 2008 American Heart Association Science Advisory on CPR (Circulation journal citation: 2008;117:2162-2167). As such, the current invention provides for advantageous periodic, uniform and continuous CPR cycles, with maximal vacuum and compression phases, as well as ventilation, all included in a five state cycle. The present CPR device invention could be used with an easily memorized verbal cue to be used by the rescuers: "pump-pump-pause". This is similar in concept to verbal cues used in dance classes, where the students are trained to use a "quick-quick-slow" step rhythm in following certain music. The "pump-pump-pause" cue could be delivered so that an approximate compression rate of 80-120 compressions per minute is delivered, in accordance to widely accepted optimal rates for CPR. Timing lights or tones could easily be incorporated to the invention, so as to aid the rescuer in the timing and cadence of the five states of the present invention, as is evident to those skilled in the electronic arts.

Returning to FIG. 5. it can be appreciated that the airway valve 200 opens at time t5 505, even though there is no leading or trailing edge of the compression sensor trace 510 at that time that could be used to trigger the airway valve 200 opening. In one embodiment of the invention, the moment of valve 200 opening at t5 can be determined by control unit 204 by keeping a timer that measures the rescuer's compression frequency and provides a delayed trigger from a feature of trace 510. In one embodiment, the control unit 204 could measure and store the time from leading edges in trace 510 at times t1 501 and t3 503, thereby establishing a time period T between compressions. The control unit could then introduce a delay of half the measured period, T/2, beginning at time t4 504, the second falling edge of trace 510. After said delay, at approximately t5 505, the control unit 204 causes the airway valve 200 to open. An advantage of this embodiment is that no assumption is made about the individual rescuer compression frequency: the compression period is automatically measured, and the timing of valve 200 opening at the start of state 405 is done accordingly. Other similar timing algorithms are possible based on various features of the sensor trace 510, which is accessible to the control unit, without departing from the scope of the invention. For example, to open the valve 200 in state 405, the control unit 204 could wait for a delay of one measured period T, beginning at time t3 503. Other similar trigger and delay techniques could be used to open the valve 200 at time t5 505. Similar techniques could be used to effect the valve closure at the end of state 405, corresponding to a new t1 time of a next cycle.

Figure 6:
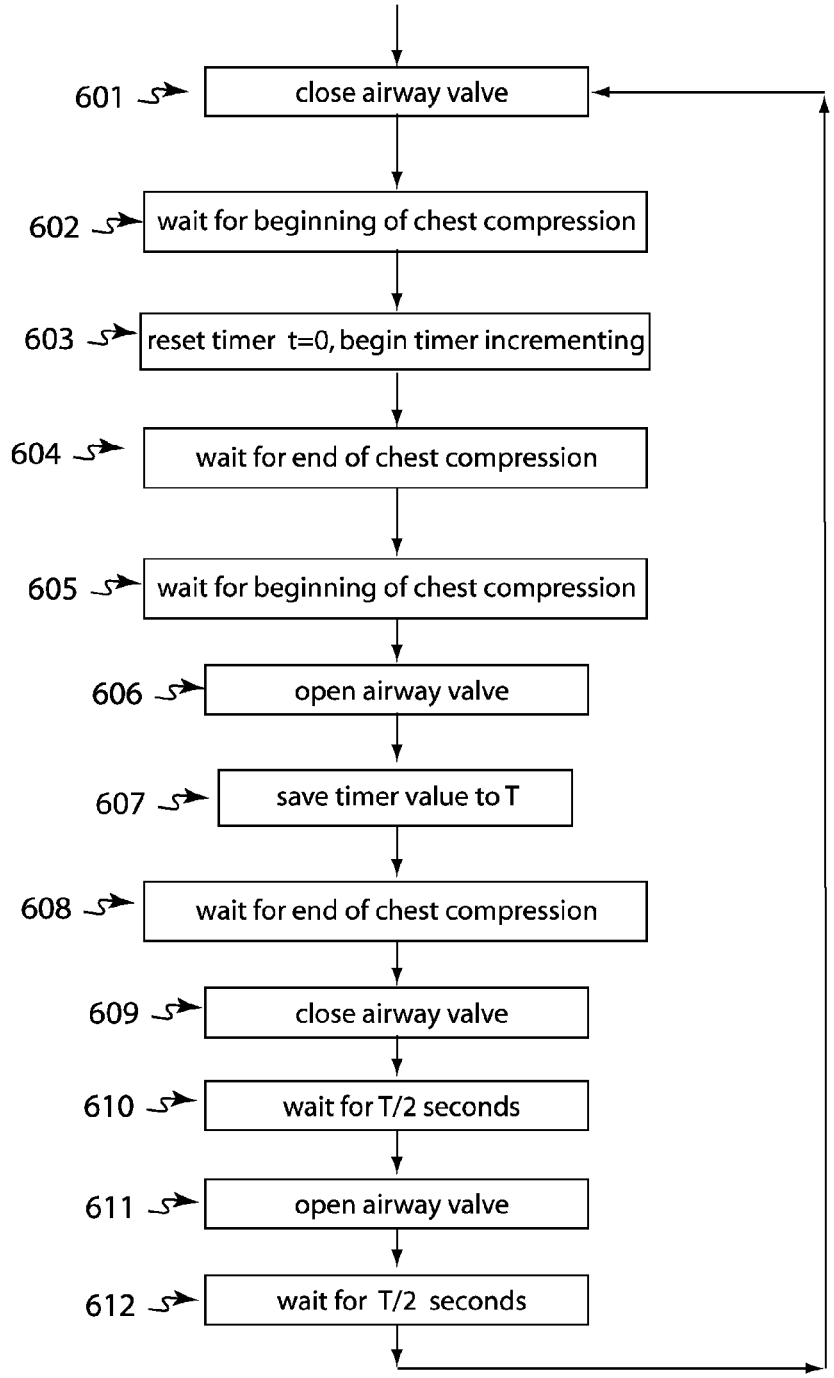
FIG. 6 shows a flow chart illustrating a control sequence used in an embodiment of the invention.

FIG. 6 shows a flow chart representing a control sequence of a microcontroller or microprocessor included in a control unit 204 (FIG. 3) of one embodiment of the invention. The control sequence shown in FIG. 6 realizes the cardio pulmonary state sequence shown in FIGS. 4A-4E and FIG. 5 by properly activating valve 200 in synchrony with the information of compressions and decompressions obtained from sensor 104 (FIG. 3). The control sequence begins at state 401 shown in FIG. 4A, by having the control sequence at step 601 with a closed airway valve. Next, the microcontroller enters a wait loop at step 602, waiting for the signal 510 (FIG. 5) from the compression sensor 104 (FIG. 3) to have a rising edge, as in time t1 501 in FIG. Such edge may be detected by the microcontroller reading an input pin, for example. Or alternatively, by having an intervening Schmitt trigger circuit as interfaces into the microcontroller sensor input, as is known in the electronic arts. Once the beginning of the first compression is detected, control passes to 603, a step in which a timer is set to zero. The timer is preferably inherent to the microcontroller in control unit 204, but may also be external to it. At this step 603, the timer is also set to begin counting the passage of time, that is, incrementing. In the next step 604, the control sequence enters a wait loop to wait for the compression to end, marking the end of state 401 at time t2 502 (FIG. 5). In the next step 605, the control sequence waits in state 402, until a compression is detected. This occurs at time t3 503 (FIG. 5), and then in the following step 606 the microcontroller provides a signal or energy to open airway valve 200, thereby implementing state 403 (FIG. 5). Also, at that instant of time t3 503, the timer value T is stored by the microcontroller in step 607. In essence the timer value T constitutes a measured period of compression frequency being delivered by rescuer 100. By using this information, proper activation of the airway valve 200 will be achieved in a manner related to the individual compression frequency. This valve activation occurs later at time t5 505, when there is no compression change, as seen in trace 510 at t5 505. After step 607, control then passes to step 608, where the end of the compression is awaited. This occurs at time t4 504, marking the end of state 403 (FIG. 5), and control passes then to step 609, in which the airway valve 200 is closed. State 404 (FIG. 5) is then begun. Proceeding to the next control step 610, said state 404 is held for a period of time T/2 (half of T), until time t5 505 (FIG. 5). Control then passes to step 611 in which the airway valve is opened, marking the beginning of state 405 (FIG. 5). Control then passes to step 612, in which a second delay of T/2 is used, establishing the duration of state 405 (FIG. 5). Incidentally, the sound of the air way valve 200 closing and opening, or only closing, can be used by the rescuer 100 to know when to begin the next compression. Alternatively, beepers, buzzers, light signals can be provided in an embodiment to indicate the beginning of the new cycle with state 401, and cueing rescuer 100 to deliver a compression. After completing step 612, control return to the original step 601, and the valve is closed in expectation of the next compression from the rescuer 100. In this way control continues as before, and the entire control sequence of FIG. 6 is repeated.

Figure 7:
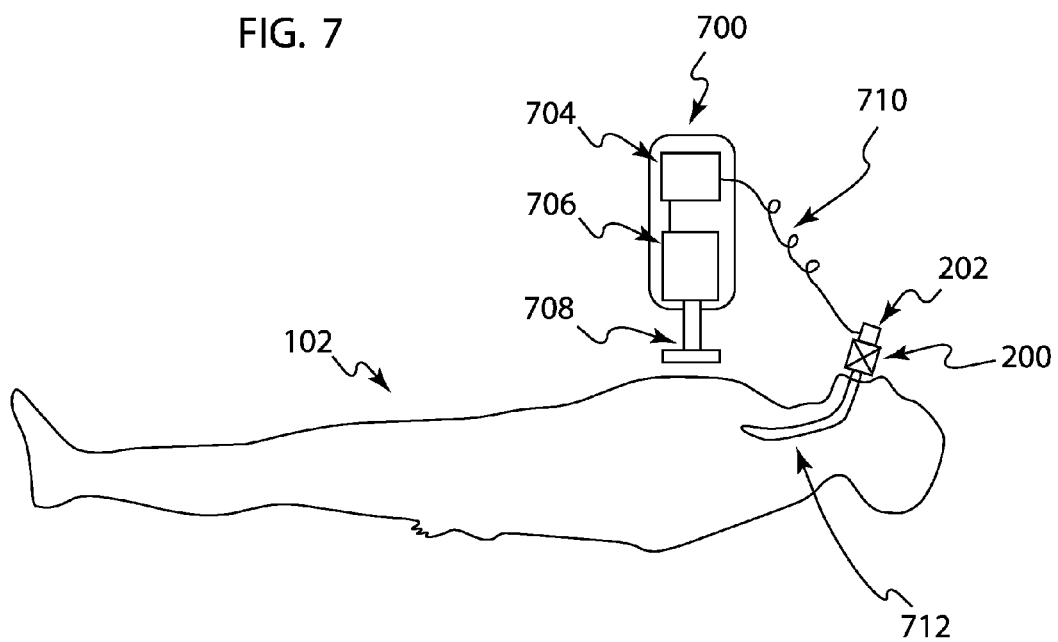
FIG. 7 shows an embodiment of the invention wherein an chest compression unit is used to deliver compressions to the patient and control the airway valve.

FIG. 7 shows an embodiment of the invention that includes a compression unit providing CPR to a patient 102. The unit provides active compressions and optionally, active decompressions, so that it functionally replaces the human rescuer. These units are well known in the art of cardiac resuscitation. One example is the "Lucas CPR (trademark) unit, manufactured by Jolife AB of Lund, Sweden. A description of such devices is given in U.S Pat. No. 7,226,427 to Steen. In essence, these mechanical chest compression units constitute means to deliver mechanical compressions to the chest of a patient, thereby relieving human rescuers from the fatigue of manually giving compressions. The unit also ensures that the timing and regularity of the compressions is kept appropriately. Relative to the present invention, FIG. 7 shows an embodiment where the airway valve previously described in this document is controlled in coordination with a compression unit, but still achieving the timing described in FIG. 5. In this embodiment of FIG. 7 however, the timing control of the valve can be achieved without the previously described compression sensor 104. This is because the control unit 704 commands the compressions, and therefore knows when the compressions are being delivered and not delivered. In this way no chest sensor is needed to know when compressions and decompressions are present, and the inventive control of the airway in synchronization with the compressions as shown in FIG. 5 can be achieved. In detail, FIG. 7 shows a CPR compression unit 700, containing a control unit 704, coupled to an actuator mechanism 706 that activates a piston plunger 708 or similar device that contacts the patient's chest, in manners known in the art of automatic CPR machines. Control unit 704 is also coupled via electric conductor 710 to airway valve actuator 202, which effects the closing and opening of valve 200, as previously described, and accordance to the timing shown in FIG. 5. In this embodiment of FIG. 7, the present invention is shown with a tracheal tube 712 as the means to control the airway of the patient. Tracheal tube 712 may include a sealing collar, or be sized to achieve a substantial airtight seal, enabling the positive and negative airway pressures of this invention, as already described. Such tracheal tube, its sealing collars and similar devices have long been known in the art. These constitute sealing means to control the airway of the patient and could have been used as well as those sealing means to control the airway of the patient such as a facemask 114 mentioned previously, or any other airway control device known in the art of ventilatory support medicine.

Figure 8:
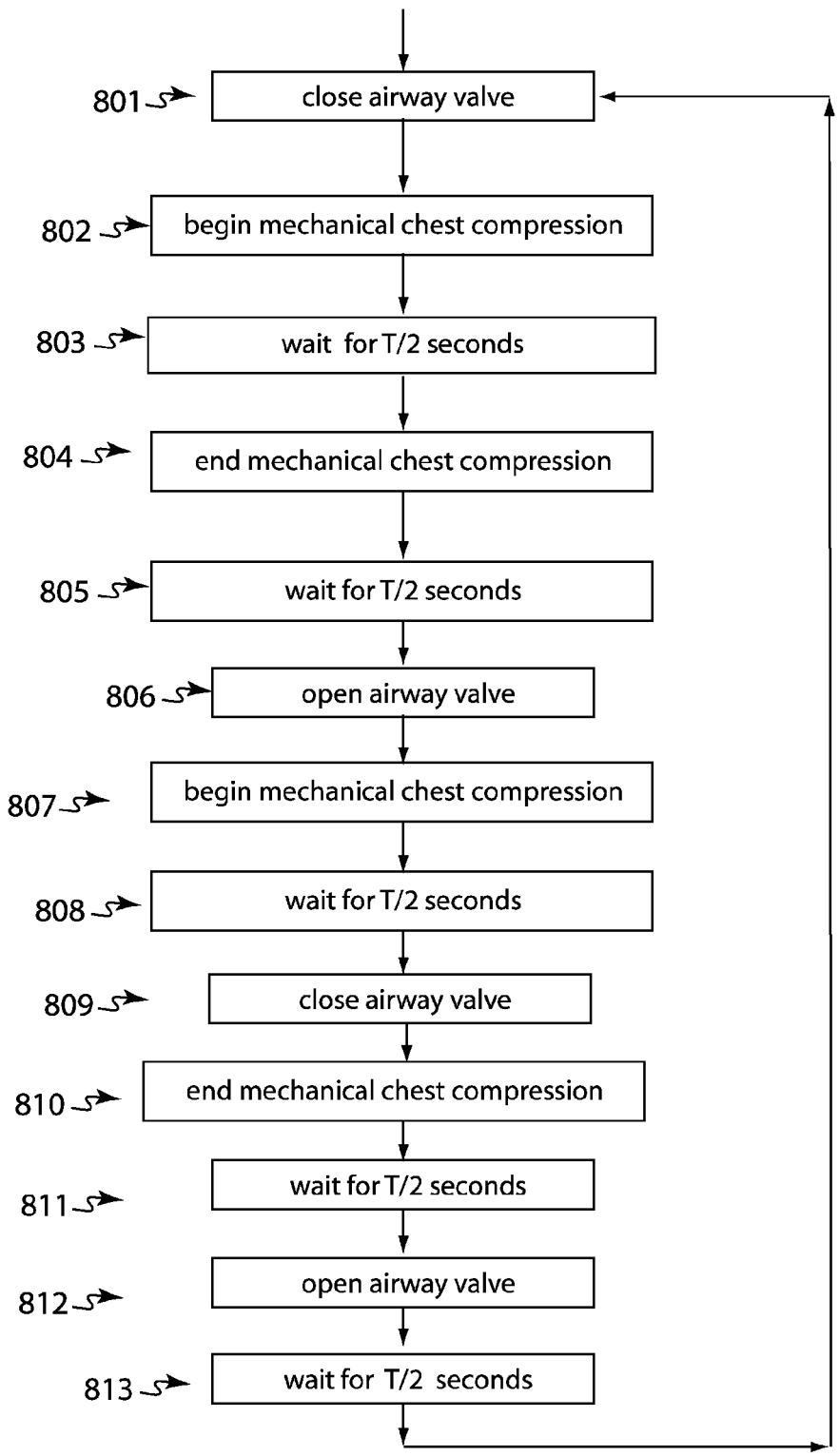
FIG. 8 shows a flow chart illustrating a control sequence used in an embodiment of the invention that includes a mechanical compression unit.

FIG. 8 shows a flow chart representing a control sequence of a microcontroller or microprocessor included in a control unit 704 of the embodiment described in FIG. 7. The control sequence shown in FIG. 8 realizes the cardio pulmonary state sequence shown in FIGS. 4A-4E and FIG. 5 by properly activating valve 200 in synchrony with the information of compressions and decompressions delivered by compression unit 700 (FIG. 7). The control sequence begins at state 401 shown in FIG. 4A, by having the control sequence at step 801 with a closed airway valve. Next, the control unit 704 commands the mechanical compressor system of actuator 706 and plunger 708 to deliver a compression in step 802. Once the beginning of the first compression is effected, control passes to 803, a step in which a timer waits for an interval of T/2 (half of T) seconds, where T is a programmed time interval between successive compressions. A typical range of values for T could be 0.3 to 0.75 seconds, in accordance to known optimal compression rates, as is known in the art of CPR. For instance, T could be programmed to 0.6 seconds. The programmed interval could be programmed once only at manufacture, or alternatively, be user programmable. The timer is preferably inherent to the microcontroller in control unit 704, but may also be external to it. In the next step 804, the control unit 704 effects the end of the mechanical compression, commanding actuator 706 to lift the plunger 708 off from the patient 102. This marks the end of state 401 at time t2 502 (FIG. 5). In the next step 805, the control sequence waits in state 402, for T/2 seconds. In step 806, the airway valve 200 is opened as before, and in step 807 a compression is initiated. This occurs at time t3 503 (FIG. 5). Control then passes to step 808, where a wait of T/2 seconds takes place. This occurs at time t4 504, marking the end of state 403 (FIG. 5), and control passes then to step 809 in which the airway valve 200 is closed, and in step 810, the compression is terminated. State 404 (FIG. 5) is then begun. Proceeding to the next control step 811, said state 404 is held for a period of time T/2, until time t5 505 (FIG. 5). Control then passes to step 812 in which the airway valve is opened, marking the beginning of state 405 (FIG. 5). Control then passes to step 813, in which a second delay interval of T/2 seconds is used, establishing the duration of state 405 (FIG. 5). After completing step 813, control returns to the original step 801, and the valve is closed in preparation for the next compression from the compression unit 700. In this way control continues as before, and the entire control sequence of FIG. 8 is repeated. It is understood that variations in the duration of the intervals described can still be present without departing from the scope of the invention.

In yet a further embodiment, and referring again to FIG. 7, the compression unit 700 includes a compression sensor (not shown) coupled mechanically to plunger 708 and electrically to control unit 704, to provide the knowledge to the microprocessor of when the compressions are actually occurring. This would allow for delays in the actual contact to the chest of the patient from the moment that a compression or decompression command is given by the control unit 704. In this embodiment, the implementation of the required steps to achieve the timing and enhancements described in FIG. 5 would be an obvious combination of the steps in FIG. 6 and FIG. 8, as will be apparent to those skilled in the firmware engineering arts.

Figure 9:
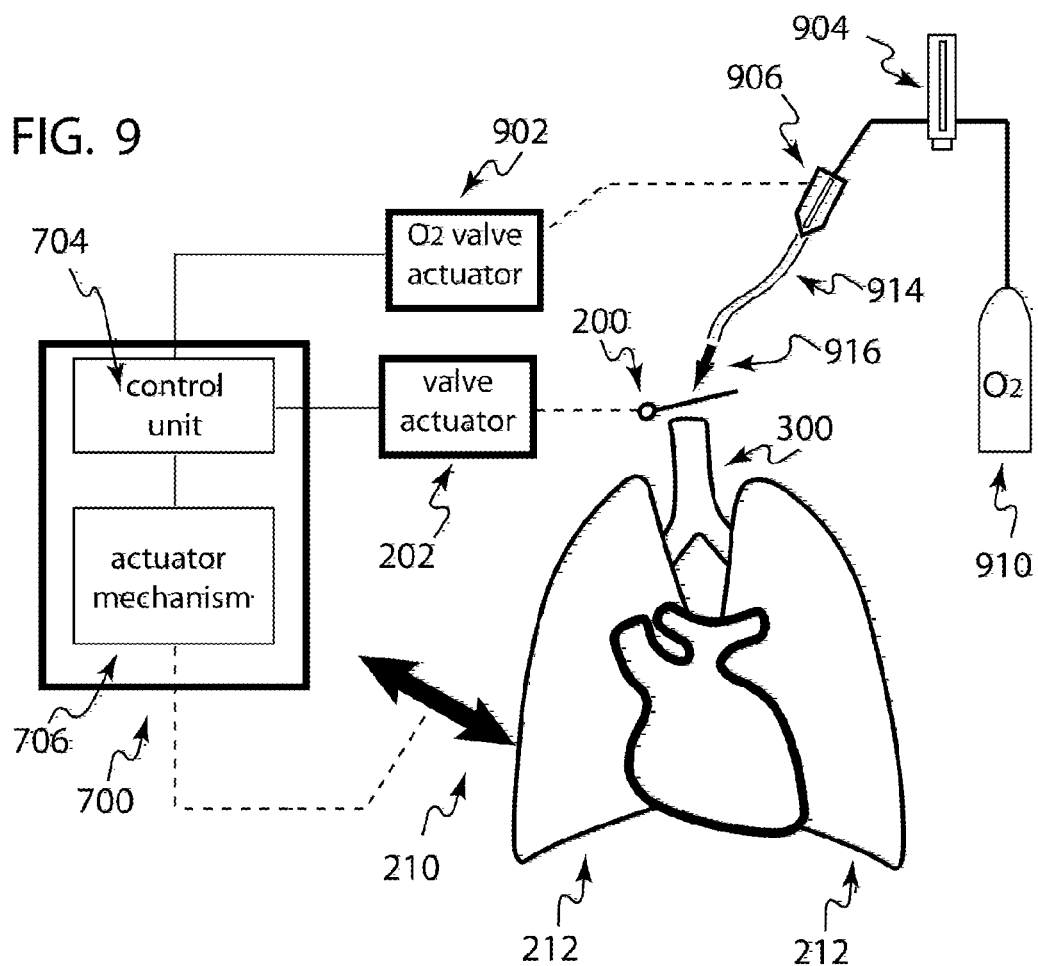
FIG. 9 shows an embodiment of the invention including a chest compression unit and with oxygen injection to provide ventilation to the patient.

In a further embodiment of the invention, shown in block diagram form in FIG. 9, the inventive system described in FIG. 7 can additionally include means to provide gases to the patient, such as oxygen. Referring to the embodiment of FIG. 9, a compression unit 700 as already described is shown. It delivers mechanical forces 210, automatically onto the chest of a patient with heart 214 and lungs 212. Compression unit 700 is constructed in a manner similar to that described for the embodiment of FIG. 7, above. Control unit 704 is implemented with a microprocessor, micro-controller, a gate array, or any such device commonly known to those skilled in the arts of firmware engineering. It can perform the inventive sequence of the invention, using programmed steps as will be further described in relation to FIG. 10. Returning to FIG. 9, Control unit 704 controls an actuator mechanism 706 that applies forces 210 to the chest of the patient. Compression unit 706 can be a pneumatic cylinder and piston system, in which case a source of compressed air would be provided in the compression unit 700. This form of mechanical compression is well known in the art of mechanical resuscitation, and an example of it is described in U.S. Pat. No. 7,226,427 to Steen. Other actuator mechanisms could include electro-mechanical mechanisms, such as a reciprocating plunger powered from an electric motor and gears, as is commonly known in the mechanical engineering field. An example of such mechanism are the reciprocating saws commonly available in hardware stores, under the name 'saws all'. In any case of mechanical actuator 706, it can be controlled electronically by control unit 704, by conventionally known means (valves, switches, relays, etc). Control unit 704 also provides control signals to airway valve actuator 202, so as to provide occlusion or opening of valve 200 and thereby manage gas flow in the airway 300 of the patient. Control unit 704 in compression unit 700 also provides control signals to oxygen valve actuator 902, which actuates oxygen valve 906. Valves 200 and 906, and their actuators 202 and 902 are components that are well known in the art of pneumatic control. A flow meter 904 provides control of the magnitude of oxygen flow that is allowed when valve 906 is open. Alternatively, this embodiment of the invention can be constructed without flowmeter 904, if valve 906 is a proportional control valve. This type of electro-mechanical valve is well known in the art of pneumatic valve control, and provide a pre-determined flow of gas in accordance to the magnitude of a voltage or current applied to its actuator 902. That controlling voltage or current would be provided by control unit 704 in this embodiment of the invention. An oxygen source 910 is connected to valve 906, via flow meter 904, or if using a proportional control valve as element 906, directly to it. Oxygen source 910 could be realized by a simple tank and pressure regulator, as employed in many oxygen therapies in medicine, or a connection port to connect to an outside oxygen source of a hospital or ambulance. Oxygen is routed to the airway of the patient via a flexible plastic or rubber line 914. Oxygen line 914 delivers the jet 916 of oxygen at the airway of the patient. This can be done in one embodiment by passive oxygen inspiration, by locating the jet 916 of oxygen at the front of airway valve 200. In this way, when the patient passively draws air into his or her chest, and valve 200 is open, oxygen jet 916 provides oxygen to the patient. This occurs in state 405 of FIG. 5, which shows a sequence of states (already described) that the embodiment of FIG. 9 realizes. As the chest recoils from a chest decompression in state 405, valve 906 in FIG. 9 is opened, allowing oxygen to flow into the airway of the patient, and inflating the lungs in preparation for state 401 of the sequence (FIG. 5). It must be noted that in this description of ventilation, 'passive' refers to the fact that oxygen is not actively forced into the patient, as occurs with positive pressure ventilation known in the art of emergency medical care (for instance, with the well known bag-mask valve or BMV system). Returning to the description of how to construct the passive inspiration in the embodiment depicted in FIG. 9, it can be accomplished by simply disposing jet 916 immediately in front of the occluding element of valve 200. It is understood by those skilled in the arts of valves, that they typically have such an occluding element, such as a diaphragm, butterfly, ball with orifice, etc. Line 914 and jet 916 can be disposed in an airway management tube, such an endrotracheal tube, or in a face-mask providing a substantial airtight seal, in any case so as to direct the jet of oxygen so it points into the airway 300 of the patient and thus improve its delivery and mixing with intratracheal and intrabronchial gases, and thereby minimize dead volume in ventilation.

An embodiment of the invention with active oxygen delivery can also be built, still maintaining the principles of enhanced circulation with the inventive sequence of the invention, explained in FIG. 5. To provide active delivery of oxygen, line 914 can be disposed into a face-mask or endrotracheal tube that is applied to airway 300 of the patient, so that jet 916 is located distally to valve 200 (not in front of it, but beyond it and closer to the patient's lungs), so as to provide a pressurized oxygen delivery state 405 in FIG. 5. In this case, the inflow of oxygen would occur during that state 405 with airway valve 200 closed, so as to permit the pressurization of the airway with oxygen proceeding from source 910, via flow meter 904 (optionally), then via valve 906 and then through line 914. This would enable the full lungs required in state 401 of the invention, shown in FIG. 5. Exhalation of body gases including carbon dioxide would occur later in the inventive sequence, in state 403 of FIG. 5, with airway valve 200 of FIG. 9 open, oxygen valve 906 closed, all this during a compression effected by actuator mechanism 706. For embodiments of the invention with active oxygen delivery as described, injection of oxygen with valve 906 open occurs during state 405, and could further occur, during state 401 in FIG. 5, as both of these actions contribute to inflating the lung and providing a positive thoracic pressure that favors blood ejection in state 401 when a chest compression is being delivered. A one way valve to prevent backflow of oxygen during this state could be placed in series with valve 906, as is known in pneumatic circuit arts.

In the above descriptions of the embodiment of FIG. 9, it is understood that control unit 704 with a program or firmware in its memory, (as is commonly known in the art of microprocessors and microcontrollers), provides the control signals above described so as to realize the inventive sequence of cardio-pulmonary states of FIG. 5, which maximize the positive and negative pressures of the airway. When such pressures are applied synchronously with the compressions, an advantageous enhancement of circulation results, as described earlier in reference to FIG. 5.

The embodiment of FIG. 9 of the invention may also include a gasp sensor to resynchronize the inventive sequence of FIG. 5 to the gasp. Gasping occurs asynchronously relative to CPR compressions, often during emergency rescue of patients who have suffered long ventilatory or cardiac arrest, and consists of a breath taken by an unconscious patient occasionally, while otherwise not breathing. A sensor of gasping can be realized by a pressure transducer disposed in the endrotracheal tube and unit 704 sensing a strong endrotracheal vacuum, which occurs during a gasp. The gasping correction logic implemented in the firmware of unit 704 could detect the gasp, and if it does not occur in temporal coincidence with the vacuum states 402 or 404 of FIG. 5, the control sequence would be reset so that the sequence would proceed to be at state 405 when the gasp is detected, opening airway valve 200, and permitting oxygen or air ingress and fill the lungs. This state of full lungs after a gasp coincides with the full lungs description given earlier in reference to FIG. 5, and thus an advantageous synchronization is realized that maintains the enhanced circulation of the invention, while minimizing its disruption by gasps. Other mechanical gasp sensors, such as a band around the chest could also be used.

The scope of the embodiment described in FIG. 9 includes the delivery of other respiratory gases, or mixtures of them, such as oxygen and carbon dioxide to help maintain normal levels of carbon dioxide in the patient when the ventilations are relatively fast, for instance. Also included in the scope of the invention is the delivery of air, appropriate in emergency situations where oxygen sources are not readily available. In this case, elements 910 and 904 of the invention could be substituted by a flexible respirator bag and valve, similar to the one used in common bag-valve-mask (BMV) systems used in conventional emergency resuscitation. This would still be in the scope of the invention, as jet 916 could be air, and valve 906 would be connected to the bag system, which would provide pressurized air to the patient. In other words, the description given above for oxygen delivery elements can describe construction of this alternate embodiment with a respirator bag, substituting the oxygen source with the respirator bag, as will be obvious to those skilled in emergency ventilation.

Figure 10:
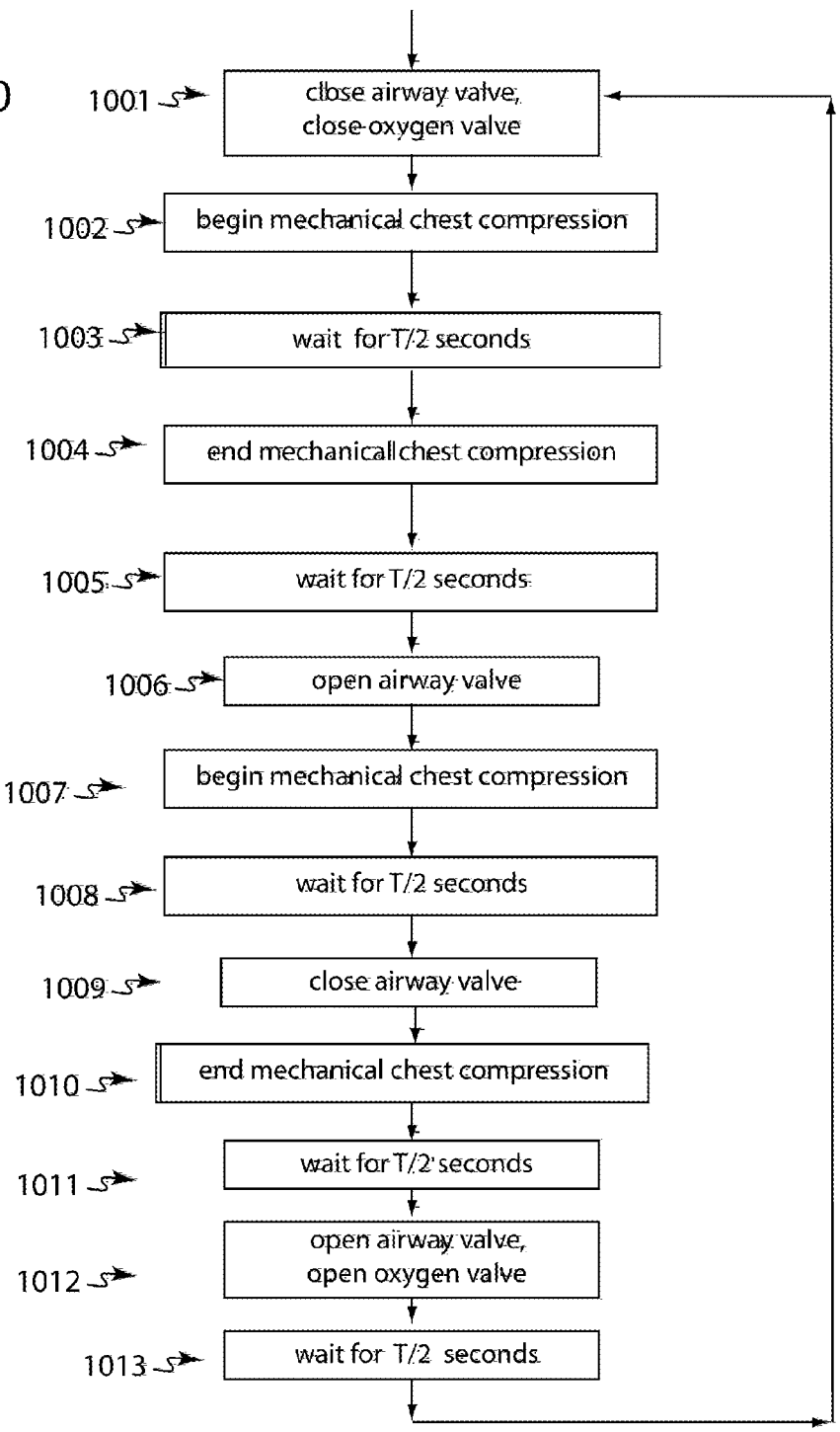
FIG. 10 shows a flow chart illustrating a control sequence used in an embodiment of the invention that includes a mechanical compression unit and oxygen delivery.

FIG. 10 shows a flow chart representing a control sequence of a microcontroller or microprocessor included in a control unit 704 of the embodiment described in FIG. 9. The control sequence shown in FIG. 10 realizes the cardio pulmonary state sequence shown in FIG. 4 and FIG. 5 by properly activating valve 200 in synchrony with the information of compressions and decompressions delivered by compression unit 700 (FIG. 9). The control sequence begins at state 401 shown in FIG. 4, by having the control sequence at step 1001 with a closed airway valve 200 and a closed oxygen valve 906. Next, the control unit 704 commands the mechanical compressor system of actuator 706 to deliver a compression. Once the beginning of the first compression is effected, control passes to 1003, a step in which a timer waits for an interval of T/2 (half of T) seconds, where T is a programmed time interval between successive compressions. A typical range of values for T could be 0.3 to 0.75 seconds, in accordance to known optimal compression rates, as is known in the art of CPR. For instance, T could be programmed to 0.6 seconds. The programmed interval could be programmed once only at manufacture, or alternatively, be user programmable. The timer is preferably inherent to the microcontroller in control unit 704, but may also be external to it. In the next step 1004, the control unit 704 effects the end of the mechanical compression, commanding actuator 706 to lift the plunger 708 off from the patient 102. This marks the end of state 401 at time t2 502 (FIG. 5). In the next step 1005, the control sequence waits in state 402, for T/2 seconds. In step 1006, the airway valve 200 is opened as before, and in step 1007 a compression is initiated. This occurs at time t3 503 (FIG. 5). Control then passes to step 1008, where a wait of T/2 seconds takes place. This occurs at time t4 504, marking the end of state 403 (FIG. 5), and control passes then to step 1009, in which the airway valve 200 is closed, and in step 1010, the compression is terminated. State 404 (FIG. 5) is then begun. Proceeding to the next control step 1011, said state 404 is held for a period of time T/2, until time t5 505 (FIG. 5). Control then passes to step 1012 in which the airway valve is opened, the oxygen valve is opened, marking the beginning of state 405 (FIG. 5) and permitting the ingress of oxygen into the patient. Control then passes to step 1013, in which a second delay interval of T/2 seconds is used, establishing the duration of state 405 (FIG. 5). After completing step 1013, control returns to the original step 1001, and the airway valve 200 and oxygen valve 906 is closed in preparation for the next compression from the compression unit 700. In this way control continues as before, and the entire control sequence of FIG. 10 is repeated. It is understood that variations in the duration of the intervals described can still be present without departing from the scope of the invention.

In yet a further embodiment, and referring again to FIG. 9 and FIG. 7, the compression unit 700 includes a compression sensor (not shown) coupled mechanically to plunger 708 and electrically to control unit 704, to provide the knowledge to the microprocessor of when the compressions are actually occurring. This would allow for delays in the actual contact to the chest of the patient from the moment that a compression or decompression command is given by the control unit 704. In this embodiment, the implementation of the required steps to achieve the timing and enhancements described in FIG. 5 would be an obvious combination of the steps in FIG. 6 and FIG. 10, as will be apparent to those skilled in the firmware engineering arts.

In closing, a description has been given of a CPR device and method that provides enhanced circulation by an optimal combination and sequencing of maximal positive and maximal negative intrathoracic pressures, while maintaining a degree of ventilation to the patient. Namely, the embodiments of the invention provide for an optimal positive thoracic pressure compression state 401, with passively or actively filled lungs, achieved by either passive chest recoil with an open airway as via state 405, or an active inflation mechanism. Said embodiments also provide for an optimal negative pressure decompression state 404, combined with actively emptied lungs (by chest compression). Further the embodiments provide for the appropriately ordered states 401, 404, and 405 that enable the optimal pressure states and open airway ventilation state of the cardio pulmonary system during repetitive CPR. Further, the embodiments include intervening states 402 and 403 that correctly set up the previously mentioned states 401, 404, and 405, by ensuring the best lung inflation level for those states. Variations of the invention are possible, with additional intervening states not described here, but in any case preserving the three basic states 401, 404, and 405 in that order, without departing from the scope of the invention.

Furthermore, the embodiments described above could be combined with ventilator machines, or combinations of ventilator and automatic CPR machines. In this case positive thoracic pressure providing greater degrees of air inflow in state 405 FIG. 5 would be possible, without departing from the scope of the invention.

The invention claimed is:

1. A cardio-pulmonary resuscitation apparatus to assist in the rescue of a patient in cardiac arrest, comprising:
    sealing means to control the airway of the patient, and
    a valve that in combination with said sealing means is configured to open and close the airway of the patient, and
    means to actuate the valve, and
    a mechanical ventilation device to actively inflate the lungs, and
    means to deliver mechanical compressions to the chest of the patient, and
    a control unit, coupled to said valve actuating means and to said mechanical ventilation device and to said mechanical compression delivery means, the control unit configured to actuate the valve, the mechanical ventilation device, and the mechanical compression delivery means, so as to effect the sequence of states consisting of:
        a) compressed chest with closed airway,
        b) decompressed chest with closed airway,
        c) compressed chest with open airway to ventilate respiratory gas out of the lungs of the patient,
        d) decompressed chest with closed airway,
        e) decompressed chest with active lung inflation to ventilate respiratory gas into the lungs of the patient.

2. A method for cardio-pulmonary resuscitation to assist in the rescue of a patient in cardiac arrest, comprising:
    providing sealing means to control the airway of the patient, and
    providing a valve that in combination with said sealing means is configured to open and close the airway of the patient, and
    providing means to actuate the valve, and
    providing a mechanical ventilation device to actively inflate the lungs, and
    providing means to deliver mechanical compressions to the chest of the patient, and
    providing a control unit, coupled to said valve actuating means and to said mechanical ventilation device and to said mechanical compression delivery means, the control unit configured to actuate the valve, the mechanical ventilation device, and the mechanical compression delivery means, so as to effect the sequence of states consisting of:
        a) compressing the chest with a closed airway,
        b) decompressing the chest with a closed airway,
        c) compressing the chest with an open airway to ventilate respiratory gas out of the lungs of the patient,
        d) decompressing the chest with a closed airway,
        e) decompressing the chest and actively inflating the lungs to ventilate respiratory gas into the lungs of the patient.

3. A cardio-pulmonary resuscitation apparatus to assist in the rescue of a patient in cardiac arrest, comprising:
    sealing means to control the airway of the patient, and
    an airway valve that in combination with said sealing means is configured to open and close the airway of the patient, and
    means to actuate the airway valve, and
    an oxygen source to provide oxygen to the patient, and
    an oxygen line to deliver oxygen at the airway of the patient, and
    an oxygen valve to control oxygen flow, and an oxygen valve actuator, and means to deliver mechanical compressions to the chest of the patient, and a control unit, coupled to said airway valve actuating means and to said oxygen valve actuator and to said mechanical compression delivery means, the control unit configured to actuate the airway valve, the oxygen valve and the mechanical compression delivery means, so as to effect the sequence of states consisting of:
   a) compressed chest with closed airway,
   b) decompressed chest with closed airway,
   c) compressed chest with open airway to ventilate respiratory gas out of the lungs of the patient,
   d) decompressed chest with closed airway,
   e) decompressed chest with the oxygen valve open to ventilate oxygen into the lungs of the patient.

4. The cardio-pulmonary resuscitation apparatus of claim 3, configured to provide passive oxygen inspiration, wherein the oxygen line is located to deliver oxygen in front of the airway valve, and wherein state e) of the sequence further includes the airway valve open.

5. The cardio-pulmonary resuscitation apparatus of claim 3, configured to provide active oxygen delivery, wherein the oxygen line is located to deliver oxygen between the airway valve and the patient's lungs, and wherein state e) of the sequence further includes the airway valve closed.

6. A cardio-pulmonary resuscitation apparatus to assist in the rescue of a patient in cardiac arrest, comprising:

sealing means to control the airway of the patient, and an airway valve that in combination with said sealing means is configured to open and close the airway of the patient, and means to actuate the airway valve, and an oxygen source to provide oxygen to the patient, and an oxygen line to deliver oxygen at the airway of the patient, and an oxygen valve to control oxygen flow, and an oxygen valve actuator, and sensor means to sense compressions on the chest of the patient, and a control unit, coupled to said airway valve actuating means and to said oxygen valve actuator and to said sensor means, the control unit configured to use the sensor information to actuate the airway valve and the oxygen valve so as to effect the sequence of states consisting of:
   a) closed airway during a sensed compression,
   b) closed airway during a sensed decompression,
   c) open airway to ventilate respiratory gas out of the lungs of the patient during a sensed compression,
   d) closed airway during a sensed decompression,
   e) open oxygen valve to ventilate oxygen into the lungs of the patient during a sensed decompression.

7. The cardio-pulmonary resuscitation apparatus of claim 6, configured to provide passive oxygen inspiration, wherein the oxygen line is located to deliver oxygen in front of the airway valve, and wherein state e) of the sequence further includes the airway valve open.

8. The cardio-pulmonary resuscitation apparatus of claim 6, configured to provide active oxygen delivery, wherein the oxygen line is located to deliver oxygen between the airway valve and the patient's lungs, and wherein state e) of the sequence further includes the airway valve closed.

9. A method for cardio-pulmonary resuscitation to assist in the rescue of a patient in cardiac arrest, comprising:

providing sealing means to control the airway of the patient, and providing an airway valve that in combination with said sealing means is configured to open and close the airway of the patient, and providing means to actuate the airway valve, and providing an oxygen source to provide oxygen to the patient, and providing an oxygen line to deliver oxygen at the airway of the patient, and providing an oxygen valve to control oxygen flow, and providing an oxygen valve actuator, and providing means to deliver mechanical compressions to the chest of the patient, and providing a control unit, coupled to said airway valve actuating means and to said oxygen valve actuator and to said mechanical compression delivery means, the control unit configured to actuate the airway valve, the oxygen valve and the mechanical compression delivery means, so as to effect the sequence of states consisting of:
   a) compressing the chest with a closed airway,
   b) decompressing the chest with a closed airway,
   c) compressing chest with an open airway to ventilate respiratory gas out of the lungs of the patient,
   d) decompressing the chest with a closed airway,
   e) decompressing the chest with the oxygen valve open to ventilate oxygen into the lungs of the patient.

10. The cardio-pulmonary resuscitation method of claim 9, delivering passive oxygen inspiration, by providing the oxygen line located to deliver oxygen in front of the airway valve, and by further opening the airway valve in state e) of the sequence.

11. The cardio-pulmonary resuscitation method of claim 9, providing active oxygen delivery, by providing the oxygen line located to deliver oxygen between the airway valve and the patient's lungs, and by further closing the airway valve in state e) of the sequence.

12. A method for cardio-pulmonary resuscitation to assist in the rescue of a patient in cardiac arrest, comprising:

providing sealing means to control the airway of the patient, and providing an airway valve that in combination with said sealing means is configured to open and close the airway of the patient, and providing means to actuate the airway valve, and providing an oxygen source to provide oxygen to the patient, and providing an oxygen line to deliver oxygen at the airway of the patient, and providing an oxygen valve to control oxygen flow, and providing an oxygen valve actuator, and providing sensor means to sense compressions on the chest of the patient, and providing a control unit, coupled to said airway valve actuating means and to said oxygen valve actuator and to said sensor means, the control unit configured to use the sensor information to actuate the airway valve and the oxygen valve, so as to effect the sequence of states consisting of:
   a) closing the airway during a sensed compression,
   b) closing the airway during a sensed decompression,
   c) opening the airway to ventilate respiratory gas out of the lungs of the patient during a sensed compression,
   d) closing the airway during a sensed decompression,
   e) opening the oxygen valve to ventilate oxygen into the lungs of the patient during a sensed decompression.

13. The cardio-pulmonary resuscitation method of claim 12, delivering passive oxygen inspiration, by providing the oxygen line located to deliver oxygen in front of the airway valve, and by further opening the airway valve in state e) of the sequence.

14. The cardio-pulmonary resuscitation method of claim 12, providing active oxygen delivery, by providing the oxygen line located to deliver oxygen between the airway valve and the patient's lungs, and by further closing the airway valve in state e) of the sequence.

* * * * *